United States Patent [19]

Zlotnik et al.

[11] Patent Number: 4,931,258
[45] Date of Patent: Jun. 5, 1990

[54] VANDAL-PROOF DEODORANT CABINET

[75] Inventors: Arnold Zlotnik; Milton Zlotnik, both of Homestead; John A. Austin, Gibsonia, all of Pa.

[73] Assignee: Surco Products, Inc., Braddock, Pa.

[21] Appl. No.: 315,344

[22] Filed: Feb. 23, 1989

[51] Int. Cl.⁵ .............................................. A61L 9/04
[52] U.S. Cl. .................................... 422/124; 239/55; 239/57; 239/60; 422/306
[58] Field of Search .................. 239/51.5, 55, 57, 60; 422/122, 124

[56] References Cited

U.S. PATENT DOCUMENTS

| 888,393 | 5/1908 | Dunning | 239/57 X |
|---|---|---|---|
| 1,254,337 | 1/1918 | Marsh | 422/124 |
| 1,885,919 | 11/1932 | Kliot | 239/57 |
| 2,942,786 | 6/1960 | Wenner et al. | 239/57 X |
| 3,522,935 | 8/1970 | Lewis | 239/57 X |
| 3,804,592 | 4/1974 | Garbe | 422/124 |
| 3,908,905 | 9/1975 | Von Philipp et al. | 239/55 |
| 3,993,444 | 11/1976 | Brown | 239/60 X |
| 4,166,087 | 8/1979 | Cline et al. | 239/60 X |
| 4,339,079 | 7/1982 | Sato et al. | 239/57 X |
| 4,396,557 | 8/1983 | DeLuca | 422/124 X |
| 4,743,406 | 5/1988 | Steiner et al. | 239/60 X |

FOREIGN PATENT DOCUMENTS

88/08721 11/1988 PCT Int'l Appl. ................ 422/124

Primary Examiner—Harold Joyce
Attorney, Agent, or Firm—Reed Smith Shaw & McClay

[57] ABSTRACT

The present invention provides a vandal-proof and theft-resistant deodorant cabinet for use in public facilities and restrooms. The housing of the deodorant cabinet is specifically designed to be removably attached to the frame of the cabinet with a series of lock tabs which are inaccessible such that the housing can only be opened by someone with a special tool. Additionally, the frame is designed to be attached to a wall by screws which are hidden from view even after the housing is removed. These features make the cabinet tamper-proof and theft-resistant while still maintaining its versatility and decorativeness.

7 Claims, 1 Drawing Sheet

VANDAL-PROOF DEODORANT CABINET

FIELD OF THE INVENTION

The present invention relates to deodorant cabinets used in public facilities and washrooms, and more specifically to vandal-proof and theft-resistant deodorant cabinets used therein.

BACKGROUND OF THE INVENTION

Deodorant cabinets have been known and used for many years. U.S. Pat. Nos. 2,234,021; 2,828,953; 3,125,407; 3,885,738; and 4,339,079 disclose a variety of different deodorant cabinets. These cabinets are suitable for use in the home since they can be easily opened. They cannot, however, be used in public facilities and restrooms since they can easily be vandalized and broken into thereby permitting the unauthorized removal of the dispersing mechanism and deodorant material located inside. While some deodorant cabinets have been said to be tamper-proof, they have been generally more complex and, therefore, more expensive to produce and more troublesome to use and maintain. Accordingly, there is a need for an inexpensive deodorant cabinet that is both vandal-proof, so as to protect the dispersing mechanism and deodorant material from loss, as well as being simple to use and easy to maintain.

U.S. Pat. No. 4,452,500 discloses a tamper-resistant deodorant cabinet. This cabinet has a cover which is hinged to a back plate and is maintained in the closed position by a latch which cooperates with a protruding member connected to a strike plate. The cabinet is opened by insertion of a key through a keyway in the cover to deflect the strike plate and disengage an engaging member from the latch. However, a variety of objects in addition to the key could be inserted through the keyway, thereby deflecting the strike plate and opening the cabinet.

It would be desirable, therefore, to provide for a vandal-proof and theft-resistant deodorant cabinet which could be used primarily in public facilities and restrooms where vandalism and theft to such devices frequently occurs.

SUMMARY OF THE INVENTION

The present invention provides a vandal-proof and theft-resistant deodorant cabinet comprising a frame capable of being fixedly mounted to a support surface and capable of containing an air freshener or deodorant and a deodorant dispersing mechanism, a housing detachably connected to the frame and a front plate attached to the housing. The housing is connected to the frame by means of a plurality of lock tabs such that the housing can only be detached from the frame by releasing the lock tabs. Preferably the frame is generally C-shaped having an integrally formed back plate, top plate and bottom plate. The lock tabs are mounted on the top and bottom plates and also on the inner surfaces of the housing near its back edge. The lock tabs on the top and bottom plates engage the lock tabs on the inner surfaces of the housing to prevent the housing from being pulled forward and removed. Only by depressing the front tip of both the top plate and the bottom plate, preferably with a special tool, can the lock tabs on both plates be shifted to permit the lock tabs on the housing to be disengaged, thereby permitting housing to be removed completely.

The deodorant cabinet of the present invention is also very versatile and can be adapted to contain many different varieties of air fresheners, deodorants and deodorant dispersing mechanisms or devices including an electric or battery operated fan, a vaporizing element, a natural evaporation deodorant, a gravity drip feed or an aerosol mechanized deodorant device. It can also be used with a variety of other dispenser features such as soap dispensers. Additionally, the front plate can have a variety of different decorative shapes and sizes while still being securely attached to the housing.

The frame used in the deodorant cabinet of the present invention also has several advantageous features. For example, it has a base tray for holding the deodorant which can easily be slid into and locked into the bottom plate of the frame. This enables the deodorant to be replaced more quickly and easily, also preventing any spillage of liquids. Additionally, the screw holes for mounting the frame to the support surface are located and hidden behind the deodorant base tray and the deodorant dispersing mechanism which further hampers vandalism or unauthorized removal of the deodorant cabinet. Additionally, the deodorant dispersing mechanisms can be slid into the frame and locked therein.

Other details, objects and advantages of the present invention will become more readily apparent from the following description of a presently preferred embodiment thereof.

BRIEF DESCRIPTION OF THE DRAWINGS

In the accompanying drawings, a preferred embodiment of the present invention is illustrated, by way of example only, wherein.

DESCRIPTION OF THE PREFERRED EMBODIMENT

Figure 1:
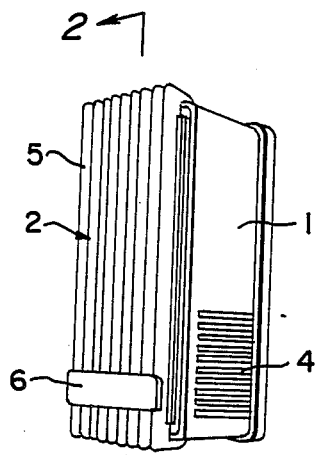
FIG. 1 shows a perspective view of a deodorant cabinet of the present invention.

FIG. 1 shows a preferred embodiment of a deodorant cabinet of the present invention. It comprises a housing 1, a front plate 2 and a frame 3 (see FIG. 5). The housing 1, front plate 2 and frame 3 can be constructed of any kind of durable, flexible and tamper-resistant material. Polypropylene is a good example of such a material. Preferably, the housing 1 is generally boxlike in shape and has a series of openings or slots 4 in the top and sides thereof to permit air to enter, mix with the deodorant and then be returned to the outside of the cabinet by a dispersing mechanism, thereby freshening the air in the washroom or public facility. The front plate 2 can be of various designs and shapes, including having decorative ridges 5 as well as a name plate 6 for the name of the user. Other designs can also be used for the front plate 2 such as a flat plate which can be etched with any pattern or adapted to receive an adhesive backed material containing a desired pattern.

Figure 2:
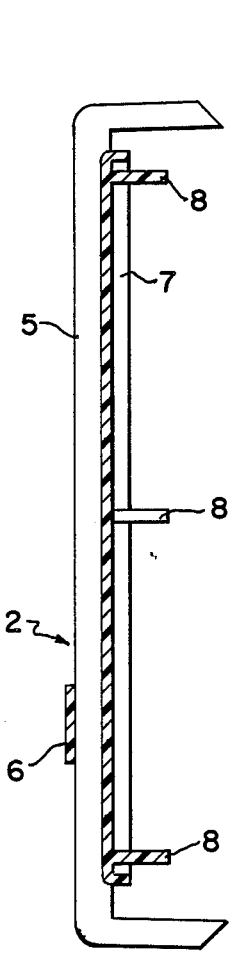
FIG. 2 shows a sectionalized side view of the front plate shown in FIG. 1 taken along line 2—2.

A portion of the front plate 2 is shown more clearly in FIG. 2. Basically, the front plate comprises a platelike section 7 and a plurality of projections 8 which fit snuggly into corresponding holes 9 in the housing 1.

Preferably, there are at least four such projections 8, one for each side of the housing 1. Once the projections 8 are placed through the holes 9, they are secured, such as by heat sealing to make the ends of the projections larger than the holes 9, so that the projections 8 cannot be pulled out. This securely fastens the front plate 2 to the housing 1. Alternatively, projections 8 may be threaded and secured through holes 9 by means of nuts. This enables the front plate 2 to be easily exchanged with one having a different design. The platelike section 7 also can comprise ridges 5 as well as name plate 6.

Figure 3:
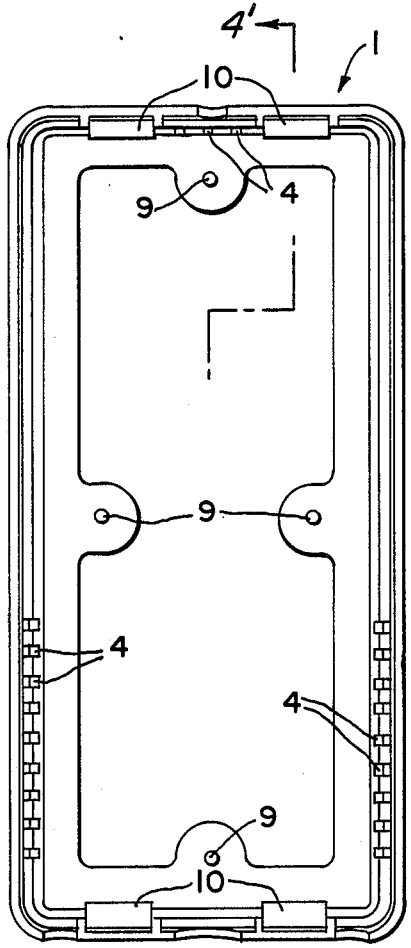
FIG. 3 shows a back view of the housing in FIG. 1 with the front plate removed.

FIG. 3 shows a back view of housing 1 of the present invention. Front plate 2 and frame 3 are not shown in this Figure. The inside of the housing 1 is hollow and is designed to easily accommodate the frame 3 which is capable of containing a variety of deodorant and deodorant dispersing mechanisms. These deodorant dispersing mechanisms can include a natural evaporator, a vaporizer element, a battery-operated fan, an electrically-operated fan or an aerosol mechanized intermittent spray device, as well as a gravity drip feed deodorant device. One deodorant dispersing mechanism, a battery-operated fan 20, is shown in FIG. 5.

The lock tabs 10 are clearly shown in FIG. 3 on the inside surfaces at the top and bottom of the housing 1. When the housing 1 is placed over the frame 3, each lock tab 10 fits snuggly against a corresponding lock tab 11 which is located on the top and bottom plates of the frame 3 (see FIG. 5). When the housing 1 is fitted into place over the frame 3, the lock tabs 10 and 11 are inaccessible to someone wanting to tamper with and open the cabinet. Preferably, a special tool is used to disengage the lock tabs 10 and 11 to permit the housing 1 to be disconnected from frame 3 and removed, thereby permitting access to the frame 3 and the deodorant and dispersing mechanism contained thereon. Preferably, the special tool is inserted through an opening in the back of the housing 1 near the bottom thereof. The tool is designed such that it reaches to the inside front of the housing 1 and presses on the front end of the bottom plate of the frame 3. This shifts the lock tabs 11 on the bottom plate and disengages them from the lock tabs 10 on the inside of the bottom of the housing 1. The same procedure is then repeated with the special tool to disengage the lock tabs on the top plate of the frame 3 so that the housing 1 may be removed completely. Preferably, there is a second set of lock tabs 12 on the top and bottom plates of the frame 3, aligned with the first set of lock tabs 11 to form a slot which receives the lock tabs 10 located on the inner surface of the housing 1. Also, lock tabs 11 are preferably sloped on one side to permit easier engagement of the lock tabs when the housing 1 is being attached to frame 3.

Figure 4:
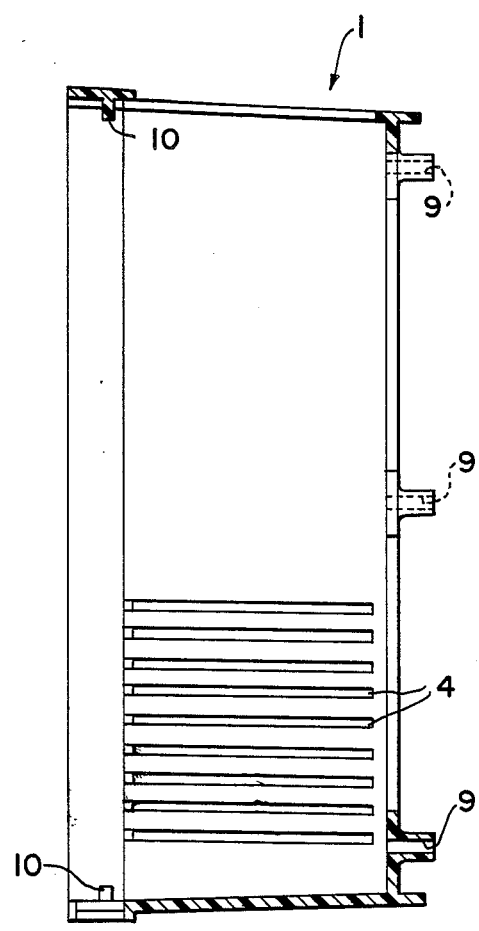
FIG. 4 is a sectionalized side view of the housing shown in FIG. 3 taken along line 4'—4'.

FIG. 4 is a side view of the housing 1 and clearly shows the holes 9 into which the projections 8 of the front plate 2 fit. Also clearly shown are the slots 4 in one side of the housing 1 which permits the circulation of air from the outside to the deodorant and deodorant dispersing device. The slots 4 in the top of the housing 1 are partially shown in FIG. 3.

Figure 5:
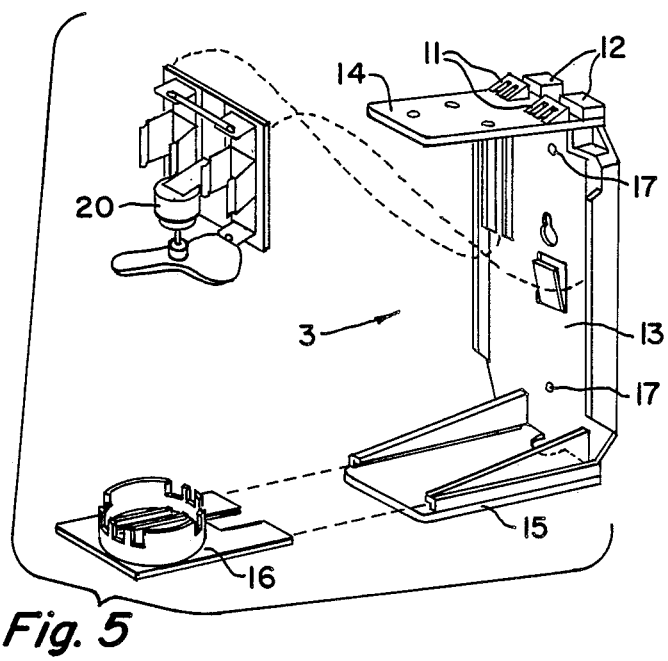
FIG. 5 shows a perspective view of the frame.

Finally, in FIG. 5, the frame 3 of the present invention is shown with its back plate 13, top plate 14 and bottom plate 15. The lock tabs can clearly be seen on the upper surface of the top plate 14. The upper surface of the bottom plate 15 is adapted to slidably receive a base tray 16 which preferably contains the deodorant. This permits the spent deodorant to be replaced very easily. The base tray 16 is multifunctional and can accept liquid deodorant canisters, square porous membrane deodorant bars or hardened cylindrical deodorant discs.

There are a plurality of openings 17 in the back plate 13 which enable the frame 3 to be fixedly mounted, such as by screws, to a support surface such as a wall. Preferably, these openings 13 are located behind the deodorant base tray and the dispersing mechanism to further inhibit tampering or unauthorized removal. The dispersing mechanism 20 can easily be slid into place and locked therein once the frame 3 is mounted to the support surface. The deodorant dispersing mechanism 20 can be attached to the back plate 13 of the frame 3 in a variety of ways known to those skilled in the art.

While a presently preferred embodiment of practicing the invention has been shown and described with particularity in connection with the accompanying drawings, the invention may otherwise be embodied within the scope of the following claims.

What is claimed:

1. A theft-resistant deodorant cabinet comprising: a frame capable of being fixedly mounted to a support surface and capable of containing a deodorant and a deodorant dispersing mechanism, a housing and a front plate attached to the housing, the housing being detachably connected to the frame by a plurality of lock tabs on the housing in one-to-one correspondence with a plurality of lock tabs on the frame, said lock tabs located on the frame forming a plurality of slots for said lock tabs located on the housing, said lock tabs on the frame and the housing being substantially inaccessible from the exterior of the cabinet such that a portion of the frame must be moved to release the lock tabs on the housing from said slots thereby enabling the housing to be detached from the frame.

2. The deodorant cabinet as described in claim 1 wherein the frame comprises a back plate, a top plate and a bottom plate and wherein the lock tabs are mounted on an inside surface of the housing, an upper surface of the top plate and a lower surface of the bottom plate.

3. The deodorant cabinet as described in claim 2 wherein a plurality of pairs of lock tabs are located on the frame and form the slot for each lock tab located on the housing.

4. The deodorant cabinet as described in claim 2 further comprising a slideable base tray capable of holding deodorant which slidably engaged the bottom plate.

5. The deodorant cabinet as described in claim 1 wherein further comprising a means for fixedly mounting the frame to the support surface, said mounting means accessible only after removal of the deodorant base tray and the deodorant dispersing mechanism.

6. The deodorant cabinet as described in claim 5 wherein the means for fixedly mounting the frame to the support surface is a screw which is hidden from view when the housing is removed from the frame.

7. The deodorant cabinet as described in claim 1 wherein the deodorant dispersing mechanism can be slid into the frame and locked therein.

* * * * *